(12) United States Patent
Nelson et al.

(10) Patent No.: US 6,849,615 B2
(45) Date of Patent: Feb. 1, 2005

(54) 13-SUBSTITUTED METHACYCLINE COMPOUNDS

(75) Inventors: Mark L. Nelson, Wellesley, MA (US); Beena Bhatia, Arlington, MA (US); Laura McIntyre, Arlington, MA (US); Glen Rennie, Weymouth, MA (US)

(73) Assignees: Paratek Pharmaceuticals, Inc., Boston, MA (US); Trustees of Tufts College, Medford, MA (US)

( * ) Notice: Subject to any disclaimer, the term of this patent is extended or adjusted under 35 U.S.C. 154(b) by 0 days.

(21) Appl. No.: 10/285,975

(22) Filed: Nov. 1, 2002

(65) Prior Publication Data

US 2003/0166952 A1 Sep. 4, 2003

Related U.S. Application Data

(63) Continuation of application No. 09/895,796, filed on Jun. 29, 2001, now Pat. No. 6,500,812.
(60) Provisional application No. 60/216,580, filed on Jul. 7, 2000, provisional application No. 60/154,701, filed on Sep. 14, 1999, provisional application No. 60/193,972, filed on Mar. 31, 2000, provisional application No. 60/143,879, filed on Mar. 3, 2000, provisional application No. 60/204,158, filed on May 15, 2000, provisional application No. 60/212,030, filed on Jun. 16, 2000, and provisional application No. 60/212,471, filed on Jun. 16, 2000.

(51) Int. Cl.$^7$ ......................... A61K 31/65; C07C 237/26
(52) U.S. Cl. ........................................ 514/152; 552/204
(58) Field of Search ........................... 552/204; 514/152

(56) References Cited

U.S. PATENT DOCUMENTS

| | | | |
|---|---|---|---|
| 2,980,584 A | 4/1961 | Hammer | 167/65 |
| 2,990,331 A | 6/1961 | Neumann et al. | 167/65 |
| 3,062,717 A | 11/1962 | Hammer | 167/65 |
| 3,165,531 A | 1/1965 | Blackwood et al. | 260/330.5 |
| 3,454,697 A | 7/1969 | Joyner et al. | 424/227 |
| 3,557,280 A | 1/1971 | Weber et al. | 424/80 |
| 3,674,859 A | 7/1972 | Beutel et al. | 424/80 |
| 3,957,980 A | 5/1976 | Noseworthy | 424/227 |
| 4,018,889 A | 4/1977 | Armstrong | 424/80 |
| 4,024,272 A | 5/1977 | Rogalski et al. | 424/275 |
| 4,126,680 A | 11/1978 | Armstrong | 424/80 |
| 5,532,227 A | 7/1996 | Golub et al. | 514/152 |
| 5,789,395 A | 8/1998 | Amin et al. | 514/152 |
| 5,834,450 A | 11/1998 | Su | 514/152 |

FOREIGN PATENT DOCUMENTS

| | | |
|---|---|---|
| GB | 1108310 | 4/1968 |
| WO | WO 01/19784 A1 | 3/2001 |

OTHER PUBLICATIONS

Comisso et al., "Synthesis, conformational studies and enantioselective homogeneous catalytic hydrogenation with CRC–PHOS, and some congeners." Croatica Chemica Acta, vol. 54(3), pp. 375–395, 1981 (abstract only).*
Berge et al. (1977) "Pharmaceutical Salts", *J. Pharm. Sci.* 66:1–19.
Miyaura et al., Palladium–catalyzed reaction of 1–alkenylboronates with vinylic halides: (1z,3e)–1–phenyl–1,3–octadiene (benzene, 1,3–octadienyl–, (z,e)–) *Organic Synthesis* 68:130–36.
Oh–e et al. (1993) "Palladium–catalyzed cross–coupling reaction of organoboron compounds with organic triflates," *J. Org. Chem.* (1993) 58:2201–8.
Silverman (1992) "The Organic Chemistry of Drug Design and Drug Action", Academic Press, Chp. 8 pp. 352–400.
Suzuki (1991) "Synthetic studies via the cross–coupling reaction of organoboron derivatives with organic halides," *Pure & Applied Chemistry* 63:419–22.
Van der Bogert et al. (1998) "Doxycycline in combination chemotherapy of a rat leukemia," *Cancer Res.*, 48:6686–6690.

* cited by examiner

*Primary Examiner*—Barbara P. Badio
(74) *Attorney, Agent, or Firm*—Lahive & Cockfield, LLP; Elizabeth A. Hanley, Esq.; Cynthia M. Soroos, Esq.

(57) ABSTRACT

13-substituted methacycline compounds, methods of treating tetracycline responsive states, and pharmaceutical compositions containing the 13-substituted methacycline compounds are described.

13 Claims, No Drawings

13-SUBSTITUTED METHACYCLINE COMPOUNDS

RELATED APPLICATIONS

This application is a continuation of U.S. application Ser. No. 09/895,796, filed Jun. 29, 2001, now U.S. Pat. No. 6,500,812 which claims priority to U.S. Provisional Application Ser. No. 60/216,580, entitled I3-Substituted Methacycline Compounds," filed on Jul. 7, 2000; the entire contents of which are hereby incorporated herein by reference. This application is also related to U.S. Provisional Application Nos. 60/154,701, filed on Sep. 14, 1999; 60/193,972, filed on Mar. 31, 2000; 60/193,879, filed on Mar. 31, 2000; 60/204,158, filed on May 15, 2000; 60/212,030, filed Jun. 16, 2000; and 60/212,471, filed Jun. 16, 2000, the entire contents of each of these applications are hereby incorporated herein by reference.

BACKGROUND OF THE INVENTION

The development of the tetracycline antibiotics was the direct result of a systematic screening of soil specimens collected from many parts of the world for evidence of microorganisms capable of producing bacteriocidal and/or bacteriostatic compositions. The first of these novel compounds was introduced in 1948 under the name chlortetracycline. Two years later, oxytetracycline became available. The elucidation of the chemical structure of these compounds confirmed their similarity and furnished the analytical basis for the production of a third member of this group in 1952, tetracycline. A new family of tetracycline compounds, without the ring-attached methyl group present in earlier tetracyclines, was prepared in 1957 and became publicly available in 1967; and minocycline was in use by 1972.

Recently, research efforts have focused on developing new tetracycline antibiotic compositions effective under varying therapeutic conditions and routes of administration. New tetracycline analogues have also been investigated which may prove to be equal to or more effective than the originally introduced tetracycline compounds. Examples include U.S. Pat. Nos. 3,957,980; 3,674,859; 2,980,584; 2,990,331; 3,062,717; 3,557,280; 4,018,889; 4,024,272; 4,126,680; 3,454,697; and 3,165,531. These patents are representative of the range of pharmaceutically active tetracycline and tetracycline analogue compositions.

Historically, soon after their initial development and introduction, the tetracyclines were found to be highly effective pharmacologically against rickettsiae; a number of gram-positive and gram-negative bacteria; and the agents responsible for lymphogranuloma venereum, inclusion conjunctivitis, and psittacosis. Hence, tetracyclines became known as "broad spectrum" antibiotics. With the subsequent establishment of their in vitro antimicrobial activity, effectiveness in experimental infections, and pharmacological properties, the tetracyclines as a class rapidly became widely used for therapeutic purposes. However, this widespread use of tetracyclines for both major and minor illnesses and diseases led directly to the emergence of resistance to these antibiotics even among highly susceptible bacterial species both commensal and pathogenic (e.g., *pneumococci* and *Salmonella*). The rise of tetracycline-resistant organisms has resulted in a general decline in use of tetracyclines and tetracycline analogue compositions as antibiotics of choice.

SUMMARY OF THE INVENTION

The invention pertains to 13-substituted methacycline compounds of the formula:

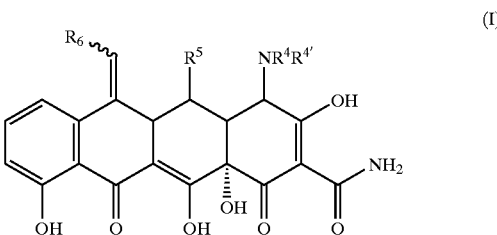

wherein:
$R^4$ and $R^{4'}$ are each alkyl;
$R^5$ is hydrogen, hydroxyl, or a prodrug moiety;
$R^6$ is a phenyl group, i.e., an alkoxyphenyl group, a halophenyl group, a carboxyphenyl group, an acylphenyl group, a cyanophenyl group, a nitrophenyl group, a naphthyl group, a dialkylphenyl group, or an alkylphenyl group; a t-butyl group; an aminoalkanethio group; and pharmaceutically acceptable salts thereof.

The invention also pertains to a method for treating a tetracycline responsive state in a mammal, by administering to a mammal a compound of formula I. In another aspect, the invention relates to the use of a compound of formula I to treat a tetracycline responsive state. The invention also pertains to pharmaceutical compositions comprising a compound of formula I, and to the use of a compound of formula I in the manufacture of a medicament to treat a tetracycline responsive state.

The invention also pertains, at least in part, to a method for synthesisizing 13-substituted methacycline compounds. The method includes contacting a methacycline compound with a boronic acid (e.g., an aryl boronic acid), under appropriate conditions such that a 13-substituted methacycline compound is formed.

In another embodiment, the invention also includes a method for the synthesis of a 13-substituted methacycline compound. The method includes contacting a methacycline compound with a tertiary alcohol, under appropriate conditions (e.g., an acid catalyst) such that a 13-substituted methacycline compound is synthesized.

DETAILED DESCRIPTION OF THE INVENTION

The invention pertains to 13-substituted methacycline compounds of the formula:

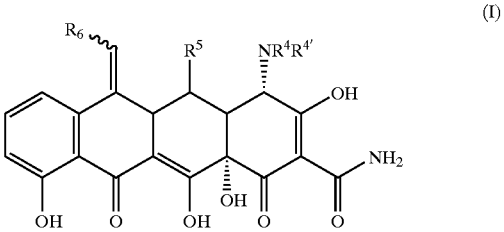

wherein:
$R^4$ and $R^{4'}$ are each alkyl;
$R^5$ is hydrogen, hydroxyl, or a prodrug moiety;
$R^6$ is a phenyl group, i.e., an alkoxyphenyl group, a halophenyl group, a carboxyphenyl group, an acylphenyl group, a cyanophenyl group, a nitrophenyl group, a naphthyl group or an alkylphenyl group; a t-butyl group; an aminoalkanethio group; and pharmaceutically acceptable salts and prodrugs thereof.

The term "13-substituted methacycline compounds" includes methacycline compounds with a substituent at the 13 position (e.g., a compound of formula I with a substituent at the $R^6$ position). In an embodiment, the substituted methacycline compound is substituted methacycline (e.g., wherein $R^4$ and $R^{4'}$ are methyl, and $R^5$ is hydroxyl).

In yet another embodiment, $R^6$ is a phenyl group, i.e., an alkoxyphenyl group, an halophenyl group, a carboxyphenyl group, an acylphenyl group, a cyanophenyl group, a nitrophenyl group, a naphthyl group or an alkylphenyl group; a t-butyl group; an aminoalkanethio group. Examples of compounds where $R^6$ is a phenyl group include 13-(phenyl) methacycline and 13-(4'-chlorophenyl-5-cyclohexanoate) methacycline.

In an embodiment, $R^6$ is an alkoxyphenyl group. Examples of such compounds include 13-(4'-methoxyphenyl) methacycline, 13-(methylenedioxyphenyl) methacycline, 13-(4'-ethoxyphenyl) methacycline, 13-(p-carbomethoxyphenyl) methacycline, and 13-(3',4'-methylenedioxyphenyl) methacycline.

In an embodiment, $R^6$ is a halophenyl group. Examples of such compounds include 13-(4'-fluorophenyl) methacycline, 13-(4'-chlorophenyl) methacycline, 13-(3'-chlorophenyl) methacycline, 13-(methylenedioxyphenyl) methacycline, 13-(3'-carboxylphenyl) methacycline, 13-(3'-4'-dichlorophenyl) methacycline, 13-(4'-acetylphenyl) methacycline, 13-(4'-ethoxyphenyl) methacycline, 13-(4'-chlorophenyl-5-cyclohexanoate) methacycline, 13-(3,5-difluorophenyl) methacycline, 13-(3+-acetylphenyl) methacycline, 13-(4'-bromophenyl) methacycline, 13-(2,4-difluorophenyl) methacycline, 13-(2-chlorophenyl) methacycline, 13-(p-carbomethoxyphenyl) methacycline, and 13-(trifluoromethylphenyl) methacycline.

In an embodiment, $R^6$ is a carboxyphenyl group. Examples of such compounds include 13-(3'-carboxylphenyl) methacycline.

In an embodiment, $R^6$ is an acylphenyl group. Examples of such compounds include 13-(3'-acetylphenyl) methacycline, 13-(4'-acetylphenyl) methacycline, and 13-(3'-formyl) methacycline.

In an embodiment, $R^6$ is a cyanophenyl group. Examples of such compounds include 13-(p-cyanophenyl) methacycline.

In an embodiment, $R^6$ is a nitrophenyl group. Examples of such compounds include 13-(4'-nitrophenyl) methacycline.

In an embodiment, $R^6$ is a naphthyl group. Examples of such compounds include 13-(naphthyl) methacycline.

In an embodiment, $R^6$ is an dialkylphenyl group. Examples of such compounds include 13-(3,5-dimethylphenyl) methacycline.

In an embodiment, $R^6$ is an alkylphenyl group. Examples of such compounds include 13-(p-t-butylphenyl) methacycline and 13-(p-tolyl) methacycline.

In an embodiment, $R^6$ is a t-butyl group. Examples of such compounds include 9,13-di-t-butyl) methacycline.

In an embodiment, $R^6$ is an aminoalkanethio group. Examples of such compounds include 13-(dimethylaminoethanethio) methacycline.

The invention also pertains, at least in part, to a method for synthesisizing a 13-substituted methacycline compound (e.g., a compound of formula I). The method includes contacting a methacycline compound with a boronic acid, under appropriate conditions such that a 13-substituted methacycline compound is formed.

The term "methacycline compound" includes compounds which can be used to synthesize 13-substituted methacycline compounds of the invention. In one embodiment, methacycline compounds include compounds of formula I wherein $R^6$ is hydrogen.

The term "appropriate conditions" includes conditions which allow for the desired reaction to take place. For example, appropriate conditions may comprise a transition metal catalyst (e.g., the boronic acid coupling) or an acid catalyst (tertiary alcohol addition). The appropriate conditions may also comprise an inert atmosphere (e.g., $N_2$, Ar, etc.) and an acceptable solvent. Furthermore, one of skill in the art use literature references to further illuminate the reactions described herein and in the Examples (e.g., *Pure & Applied Chemistry*, (1991) 63:419–22; *J. Org. Chem.* (1993) 58:2201; *Organic Synthesis* 68:130).

The term "transition metal catalyst" includes transition metals and catalysts comprising a transition metal, e.g., including elements 21 through 29, 39 through 47, 57 through 79, and 89 on. Examples of transition metal catalysts include $CuCl_2$, copper (I) triflate, copper thiophene chloride, palladium (II) chloride, organopalladium catalysts such as palladium acetate, $Pd(PPh_3)_4$, $Pd(AsPh_3)_4$, $PdCl_2(PhCN)_2$, $PdCl_2$ $(Ph_3P)_2$, $Pd_2(dba)_3—CHCl_3$ ("dba" = dibenzylacetone); and combinations thereof. Other transition metal catalysts include those containing metals such as rhodium (e.g. rhodium (II) acetate and $Rh_6(CO)_{16}$), iron, iridium, chromium, zirconium, and nickel. A skilled artisan will be able to select the appropriate transition metal catalyst to perform the desired reaction, based on the existing literature (see, for example, Lipshutz, B. H. *Org. React.* 1992, 41:135, incorporated herein by reference.)

The 13-substituted compounds of the invention can be synthesized by methods known in the art and/or as described herein. In Scheme 1, a general synthetic scheme for the synthesis of 13-substituted methacycline compounds is shown. In this reaction, methacycline is coupled with a boronic acid in the presence of a transition metal catalyst. Furthermore, other aryl coupling reactions known in the art may also be used.

SCHEME 1

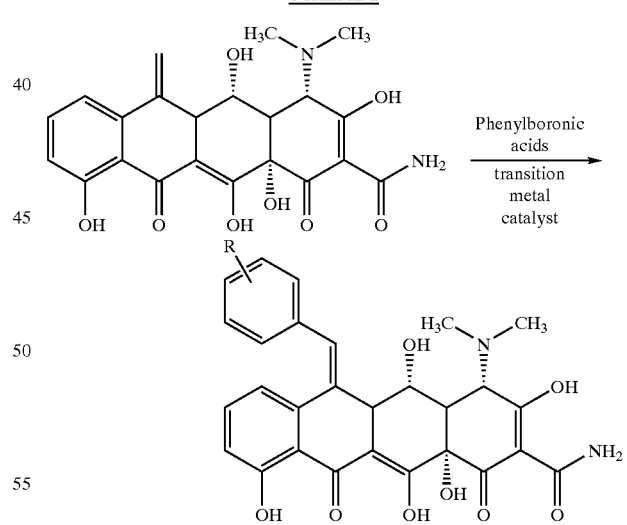

As shown in Scheme 1, the methacycline is reacted with a phenylboronic acid in the presence of a palladium catalyst such as $Pd(OAc)_2$. The resulting compound can then be purified using techniques known in the art such as preparative HPLC and characterized. The synthesis of the compounds of the invention are described in more detail in Example 1.

13-substituted methacycline compounds wherein $R^6$ is an alkyl group can be synthesized using a tertiary alcohol and an acid catalyst as shown in Scheme 2.

SCHEME 2

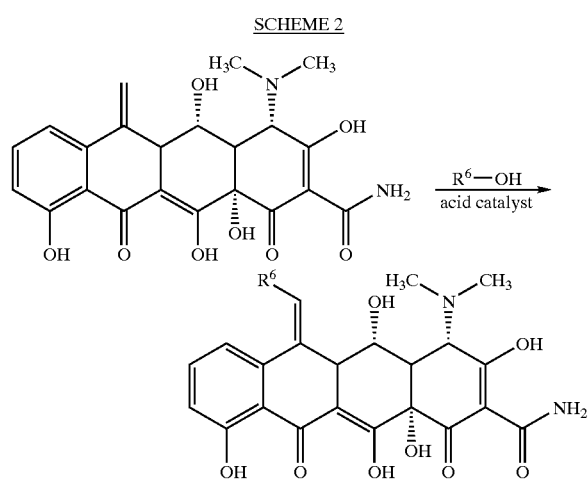

The invention also pertains to a method for synthesizing a 13-substituted methacycline compound, (e.g., a 13-alkyl substituted methacycline compound, e.g., a compound of formula (I) wherein $R^6$ is alkyl). The method includes contacting a methacycline compound with a tertiary alcohol, under appropriate conditions such that a 13-substituted methacycline compound is synthesized.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. The term alkyl further includes alkyl groups, which comprise oxygen, nitrogen, sulfur or phosphorous atoms replacing one or more carbons of the hydrocarbon backbone. In certain embodiments, a straight chain or branched chain alkyl has 6 or fewer carbon atoms in its backbone (e.g., $C_1$–$C_6$ for straight chain, $C_3$–$C_6$ for branched chain), and more preferably 4 or fewer. Likewise, preferred cycloalkyls have from 3–8 carbon atoms in their ring structure, and more preferably have 5 or 6 carbons in the ring structure. The term $C_1$–$C_6$ includes alkyl groups containing 1 to 6 carbon atoms.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)). The term "alkyl" also includes the side chains of natural and unnatural amino acids.

The term "aryl" includes groups with aromaticity, including 5- and 6-membered single-ring aromatic groups that may include from zero to four heteroatoms as well as multicyclic systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a multicyclic system (e.g., tetralin, methylenedioxyphenyl).

The term "alkenyl" includes unsaturated aliphatic groups analogous in length and possible substitution to the alkyls described above, but that contain at least one double bond.

For example, the term "alkenyl" includes straight-chain alkenyl groups (e.g., ethenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups which include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$–$C_6$ for straight chain, $C_3$–$C_6$ for branched chain). Likewise, cycloalkenyl groups may have from 3–8 carbon atoms in their ring structure, and more preferably have 5 or 6 carbons in the ring structure. The term $C_2$–$C_6$ includes alkenyl groups containing 2 to 6 carbon atoms.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups which include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$–$C_6$ for straight chain, $C_3$–$C_6$ for branched chain). The term $C_2$–$C_6$ includes alkynyl groups containing 2 to 6 carbon atoms.

Moreover, the term alkynyl includes both "unsubstituted alkynyls" and "substituted alkynyls", the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2–5 carbon atoms.

The term "acyl" includes compounds and moieties which contain the acyl radical ($CH_3CO$—) or a carbonyl group. The term "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "aroyl" includes compounds and moieties with an aryl or heteroaromatic moiety bound to a carbonyl group. Examples of aroyl groups include phenylcarboxy, naphthyl carboxy, etc.

The terms "alkoxyalkyl", "alkylaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "amine" or "amino" includes compounds where a nitrogen atom is covalently bonded to at least one carbon or heteroatom. The term "alkylamino" includes groups and compounds wherein the nitrogen is bound to at least one additional alkyl group. The term "dialkylamino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amide" or "aminocarboxy" includes compounds or moieties which contain a nitrogen atom which is bound to the carbon of a carbonyl or a thiocarbonyl group. The term includes "alkaminocarboxy" groups which include alkyl, alkenyl, or alkynyl groups bound to an amino group bound to a carboxy group. It includes arylaminocarboxy groups which include aryl or heteroaryl moieties bound to an amino group which is bound to the carbon of a carbonyl or thiocarbonyl group. The terms "alkylaminocarboxy," "alkenylaminocarboxy," "alkynylaminocarboxy," and "arylaminocarboxy" include moieties wherein alkyl, alkenyl, alkynyl and aryl moieties, respectively, are bound to a nitrogen atom which is in turn bound to the carbon of a carbonyl group.

The term "carbonyl" or "carboxy" includes compounds and moieties which contain a carbon connected with a double bond to an oxygen atom. Examples of moieties which contain a carbonyl include aldehydes, ketones, carboxylic acids, amides, esters, anhydrides, etc.

The term "thiocarbonyl" or "thiocarboxy" includes compounds and moieties which contain a carbon connected with a double bond to a sulfur atom.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O.

The term "halogen" includes fluorine, bromine, chlorine, iodine, etc. The term "perhalogenated" generally refers to a moiety wherein all hydrogens are replaced by halogen atoms.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings. Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminocarbonyl, aralkylaminocarbonyl, alkenylaminocarbonyl, alkylcarbonyl, arylcarbonyl, aralkylcarbonyl, alkenylcarbonyl, aminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Examples of heteroatoms include nitrogen, oxygen, sulfur and phosphorus.

It will be noted that the structure of some of the compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

Prodrugs are compounds which are converted in vivo to active forms (see, e.g., R. B. Silverman, 1992, "The Organic Chemistry of Drug Design and Drug Action", Academic Press, Chp. 8). Prodrugs can be used to alter the biodistribution (e.g., to allow compounds which would not typically enter the reactive site of the protease) or the pharmacokinetics for a particular compound. For example, a hydroxyl group, can be esterified, e.g., with a carboxylic acid group to yield an ester. When the ester is administered to a subject, the ester is cleaved, enzymatically or non-enzymatically, reductively or hydrolytically, to reveal the hydroxyl group.

The term "prodrug moiety" includes moieties which can be metabolized in vivo to a hydroxyl group and moieties which may advantageously remain esterified in vivo. Preferably, the prodrugs moieties are metabolized in vivo by esterases or by other mechanisms to hydroxyl groups or other advantageous groups. Examples of prodrugs and their uses are well known in the art (See, e.g., Berge et al. (1977) "Pharmaceutical Salts", J. Pharm. Sci. 66:1–19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters.

The invention also features a method for treating a tetracycline compound responsive state in a subject, by administering to the subject a 13-substituted methacycline compound of the invention, e.g., a compound of formula I. Preferably, an effective amount of the tetracycline compound is administered. Examples of 13-substituted methacycline compounds include 13-(phenyl) methacycline, 13-(4'-chlorophenyl-5-cyclohexanoate) methacycline, 13-(4'-methoxyphenyl) methacycline, 13-(methylenedioxyphenyl) methacycline, 13-(4'-ethoxyphenyl) methacycline, 13-(p-carbomethoxyphenyl) methacycline, 13-(3',4'-methylenedioxyphenyl) methacycline, 13-(4'-fluorophenyl) methacycline, 13-(4'-chlorophenyl) methacycline, 13-(3'-chlorophenyl) methacycline, 13-(methylenedioxyphenyl) methacycline, 13-(3'-carboxylphenyl) methacycline, 13-(3'-4'-dichlorophenyl) methacycline, 13-(4'-acetylphenyl) methacycline, 13-(4'-ethoxyphenyl) methacycline, 13-(4'-chlorophenyl-5-cyclohexanoate) methacycline, 13-(3,5-difluorophenyl) methacycline, 13-(3'-acetylphenyl) methacycline, 13-(4'-bromophenyl) methacycline, 13-(2,4-difluorophenyl) methacycline, 13-(2-chlorophenyl) methacycline, 13-(p-carbomethoxyphenyl) methacycline, 13-(trifluoromethylphenyl) methacycline, 13-(3'-carboxylphenyl) methacycline, 13-(3'-acetylphenyl) methacycline, 13-(4'-acetylphenyl) methacycline, 13-(3'-formyl) methacycline, 13-(p-cyanophenyl) methacycline, 13-(4'-nitrophenyl) methacycline, 13-(naphthyl) methacycline, 13-(p-t-butylphenyl) methacycline, 13-((3,5-dimethylphenyl) methacycline, 13-(p-tolyl) methacycline, 9,13-(di-t-butyl) methacycline, 13-(dimethylaminoethanethio) methacycline. Table 1 depicts the structures of many of these compounds.

TABLE 1
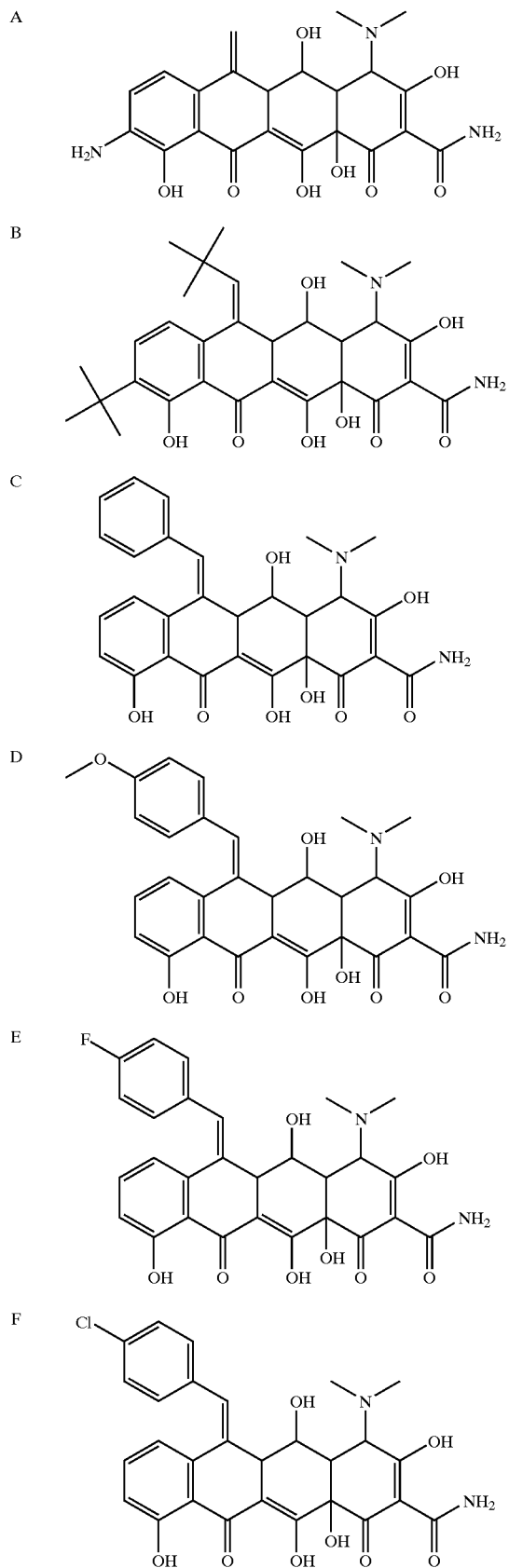
TABLE 1-continued
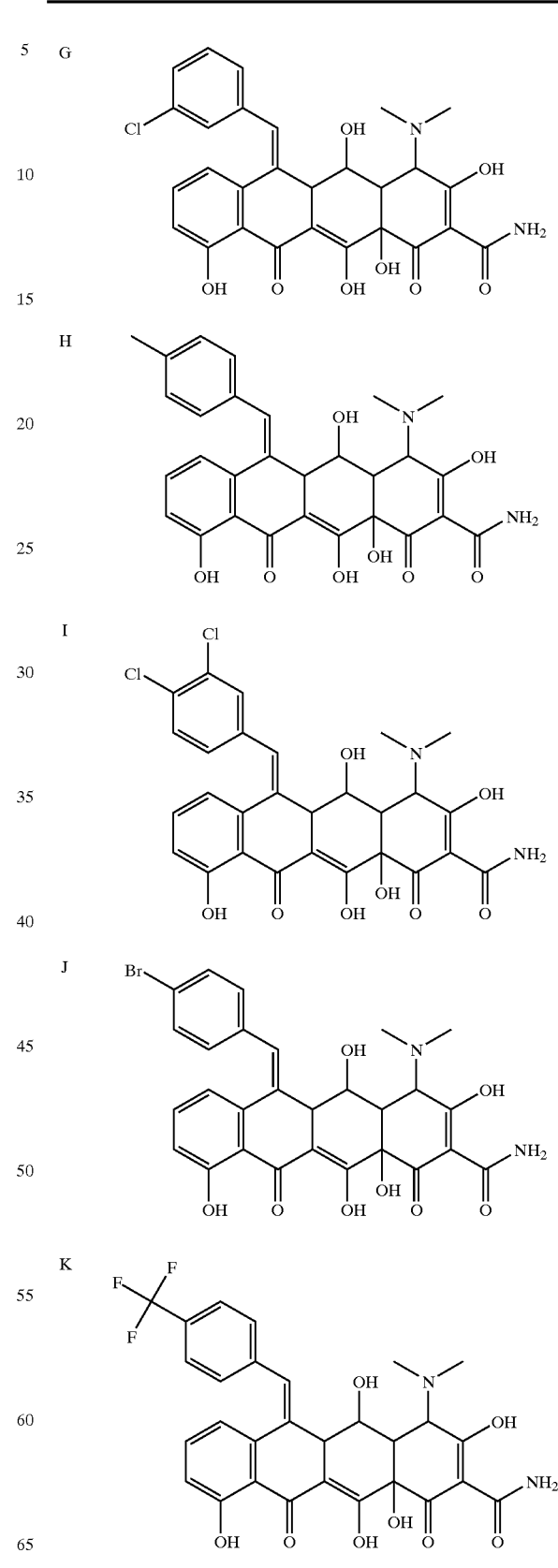

TABLE 1-continued
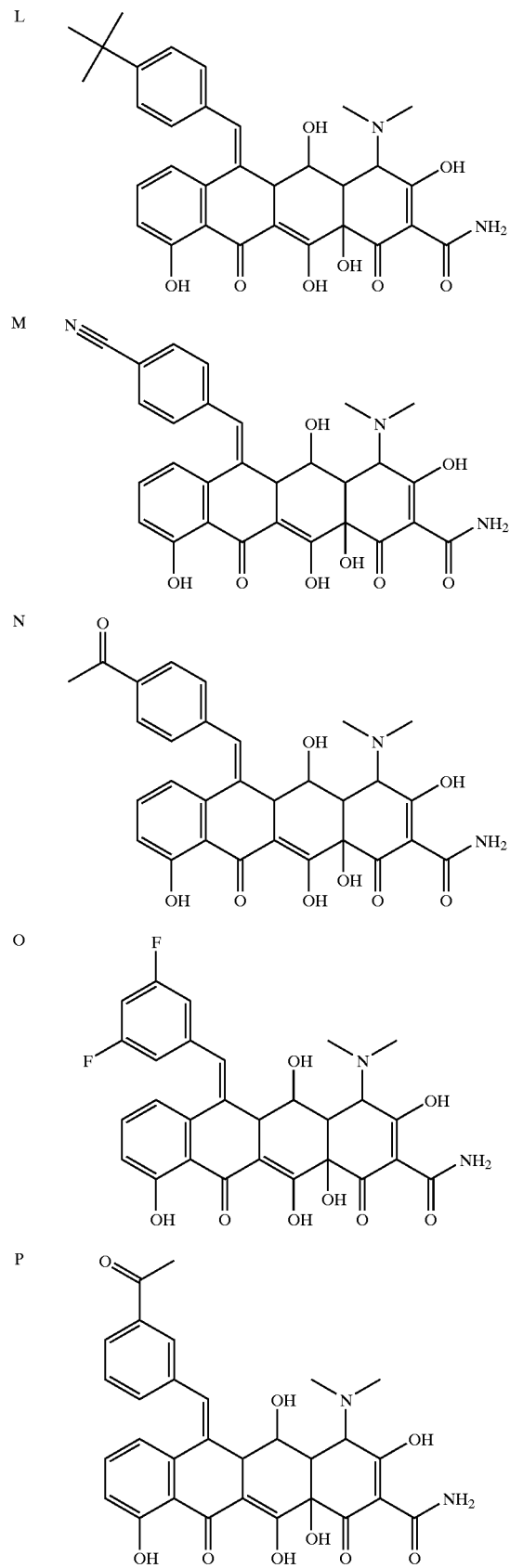
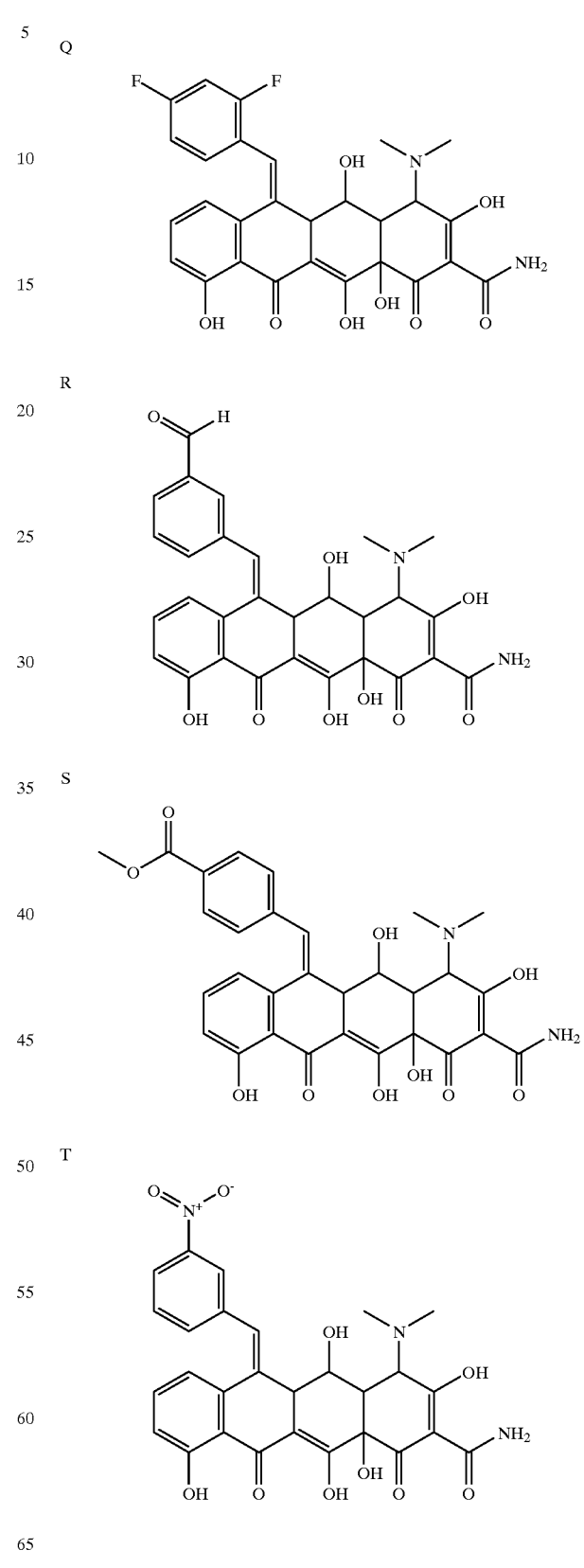

TABLE 1-continued

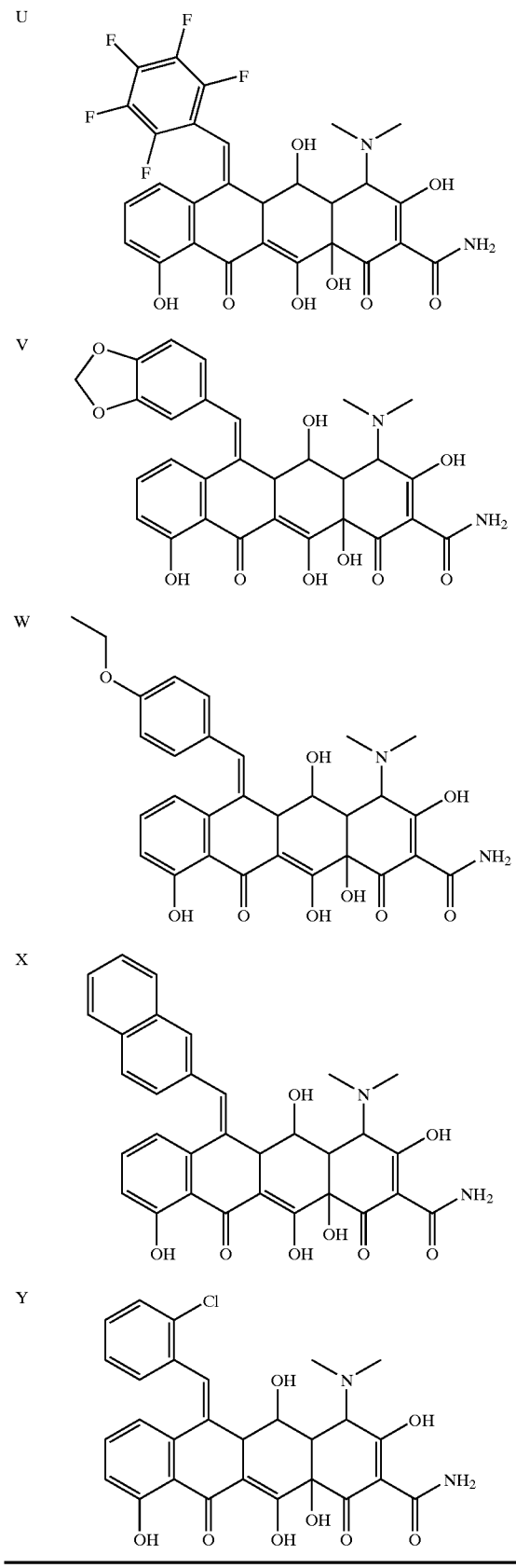

The language "tetracycline compound responsive state" includes states which can be treated, prevented, or otherwise ameliorated by the administration of a tetracycline compound of the invention. Tetracycline compound responsive states include bacterial infections (including those which are resistant to other tetracycline compounds), cancer, diabetes, and other states for which tetracycline compounds have been found to be active (see, for example, U.S. Pat. Nos. 5,789,395; 5,834,450; and 5,532,227). Compounds of the invention can be used to prevent or control important mammalian and veterinary diseases such as diarrhea, urinary tract infections, infections of skin and skin structure, ear, nose and throat infections, wound infection, mastitis and the like. In addition, methods for treating neoplasms using tetracycline compounds of the invention are also included (van der Bozert et al., Cancer Res., 48:6686–6690 (1988)).

Bacterial infections may be caused by a wide variety of gram positive and gram negative bacteria. The compounds of the invention are useful as antibiotics against organisms which are resistant to other tetracycline compounds. The antibiotic activity of the tetracycline compounds of the invention may be determined using the method discussed in Example 2, or by using the in vitro standard broth dilution method described in Waitz, J. A., National Commission for Clinical Laboratory Standards, Document M7-A2, vol. 10, no. 8, pp. 13–20, $2^{nd}$ edition, Villanova, Pa. (1990).

The tetracycline compounds may also be used to treat infections traditionally treated with tetracycline compounds such as, for example, rickettsiae; a number of gram-positive and gram-negative bacteria; and the agents responsible for lymphogranuloma venereum, inclusion conjunctivitis, psittacosis. The tetracycline compounds may be used to treat infections of, e.g., K. pneumoniae, Salmonella, E. hirae, A. baumanii, B. catarrhalis, H. influenzae, P. aeruginosa, E. faecium, E. coli, S. aureus or E. faecalis. In one embodiment, the tetracycline compound is used to treat a bacterial infection that is resistant to other tetracycline antibiotic compounds. The tetracycline compound of the invention may be administered with a pharmaceutically acceptable carrier.

The language "effective amount" of the compound is that amount necessary or sufficient to treat or prevent a tetracycline compound responsive state. The effective amount can vary depending on such factors as the size and weight of the subject, the type of illness, or the particular tetracycline compound. For example, the choice of the tetracycline compound can affect what constitutes an "effective amount". One of ordinary skill in the art would be able to study the aforementioned factors and make the determination regarding the effective amount of the tetracycline compound without undue experimentation.

The invention also pertains to methods of treatment against microorganism infections and associated diseases. The methods include administration of an effective amount of one or more tetracycline compounds to a subject. The subject can be either a plant or, advantageously, an animal, e.g., a mammal, e.g., a human.

In the therapeutic methods of the invention, one or more tetracycline compounds of the invention may be administered alone to a subject, or more typically a compound of the invention will be administered as part of a pharmaceutical composition in mixture with conventional excipient, i.e., pharmaceutically acceptable organic or inorganic carrier substances suitable for parenteral, oral or other desired administration and which do not deleteriously react with the active compounds and are not deleterious to the recipient thereof.

In one embodiment, the pharmaceutical composition comprises a 13-substituted methacycline compound of the invention, e.g., of formula I. In a further embodiment, the 13-substituted methacycline compound is 13-(phenyl) methacycline, 13-(4'-chlorophenyl-5-cyclohexanoate) methacycline, 13-(4'-methoxyphenyl) methacycline, 13-(methylenedioxyphenyl) methacycline, 13-(4'-ethoxyphenyl) methacycline, 13-(p-carbomethoxyphenyl) methacycline, 13-(3',4'-methylenedioxyphenyl) methacycline, 13-(4'-fluorophenyl) methacycline, 13-(4'-chlorophenyl) methacycline, 13-(3'-chlorophenyl) methacycline, 13-(methylenedioxyphenyl) methacycline, 13-(3'-carboxylphenyl) methacycline, 13-(3'-4'-dichlorophenyl) methacycline, 13-(4'-acetylphenyl) methacycline, 13-(4'-ethoxyphenyl) methacycline, 13-(4'-chlorophenyl-5-cyclohexanoate) methacycline, 13-(3,5-difluorophenyl) methacycline, 13-(3'-acetylphenyl) methacycline, 13-(4'-bromophenyl) methacycline, 13-(2,4-difluorophenyl) methacycline, 13-(2-chlorophenyl) methacycline, 13-(p-carbomethoxyphenyl) methacycline, 13-(trifluoromethylphenyl) methacycline, 13-(3'-carboxylphenyl) methacycline, 13-(3'-acetylphenyl) methacycline, 13-(4'-acetylphenyl) methacycline, 13-(3'-formyl) methacycline, 13-(p-cyanophenyl) methacycline, 13-(4'-nitrophenyl) methacycline, 13-(naphthyl) methacycline, 13-(p-t-butylphenyl) methacycline, 13-(3,5-dimethylphenyl) methacycline, 13-(p-tolyl) methacycline, 9,13-(di-t-butyl) methacycline, and 13-(dimethylaminoethanethio) methacycline. Table 1 depicts the structures of many of these compounds.

The language "pharmaceutically acceptable carrier" includes substances capable of being coadministered with the tetracycline compound(s), and which allow both to perform their intended function, e.g., treat or prevent a tetracycline compound responsive state. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds of the invention.

The tetracycline compounds of the invention that are basic in nature are capable of forming a wide variety of salts with various inorganic and organic acids. The acids that may be used to prepare pharmaceutically acceptable acid addition salts of the tetracycline compounds of the invention that are basic in nature are those that form non-toxic acid addition salts, i.e., salts containing pharmaceutically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and palmoate [i.e., 1,1'-methylene-bis-(2-hydroxy-3-naphthoate)] salts. Although such salts must be pharmaceutically acceptable for administration to a subject, e.g., a mammal, it is often desirable in practice to initially isolate a tetracycline compound of the invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The preparation of other tetracycline compounds of the invention not specifically described in the foregoing experimental section can be accomplished using combinations of the reactions described above that will be apparent to those skilled in the art.

The preparation of other tetracycline compounds of the invention not specifically described in the foregoing experimental section can be accomplished using combinations of the reactions described above that will be apparent to those skilled in the art.

The tetracycline compounds of the invention that are acidic in nature are capable of forming a wide variety of base salts. The chemical bases that may be used as reagents to prepare pharmaceutically acceptable base salts of those tetracycline compounds of the invention that are acidic in nature are those that form non-toxic base salts with such compounds. Such non-toxic base salts include, but are not limited to those derived from such pharmaceutically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines. The pharmaceutically acceptable base addition salts of tetracycline compounds of the invention that are acidic in nature may be formed with pharmaceutically acceptable cations by conventional methods. Thus, these salts may be readily prepared by treating the tetracycline compound of the invention with an aqueous solution of the desired pharmaceutically acceptable cation and evaporating the resulting solution to dryness, preferably under reduced pressure. Alternatively, a lower alkyl alcohol solution of the tetracycline compound of the invention may be mixed with an alkoxide of the desired metal and the solution subsequently evaporated to dryness.

The preparation of other tetracycline compounds of the invention not specifically described in the foregoing experimental section can be accomplished using combinations of the reactions described above that will be apparent to those skilled in the art.

The tetracycline compounds of the invention and pharmaceutically acceptable salts thereof can be administered via either the oral, parenteral or topical routes. In general, these compounds are most desirably administered in effective dosages, depending upon the weight and condition of the subject being treated and the particular route of administration chosen. Variations may occur depending upon the species of the subject being treated and its individual response to said medicament, as well as on the type of pharmaceutical formulation chosen and the time period and interval at which such administration is carried out.

The pharmaceutical compositions of the invention may be administered alone or in combination with other known compositions for treating tetracycline responsive states in a mammal. Preferred mammals include pets (e.g., cats, dogs, ferrets, etc.), farm animals (cows, sheep, pigs, horses, goats, etc.), lab animals (rats, mice, monkeys, etc.), and primates (chimpanzees, humans, gorillas). The language "in combination with" a known composition is intended to include simultaneous administration of the composition of the invention and the known composition, administration of the composition of the invention first, followed by the known composition and administration of the known composition first, followed by the composition of the invention. Any of the therapeutically composition known in the art for treating tetracycline responsive states can be used in the methods of the invention.

The compounds of the invention may be administered alone or in combination with pharmaceutically acceptable carriers or diluents by any of the routes previously mentioned, and the administration may be carried out in single or multiple doses. For example, the novel therapeutic agents of this invention can be administered advantageously in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration (including intraperitoneal, subcutaneous, intravenous, intradermal or intramuscular injection), solutions of a therapeutic compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. For parenteral application, examples of suitable preparations include solutions, preferably oily or aqueous solutions as well as suspensions, emulsions, or implants, including suppositories. Therapeutic compounds may be formulated in sterile form in multiple or single dose formats such as being dispersed in a fluid carrier such as sterile physiological saline or 5% saline dextrose solutions commonly used with injectables.

Additionally, it is also possible to administer the compounds of the present invention topically when treating inflammatory conditions of the skin. Examples of methods of topical administration include transdermal, buccal or sublingual application. For topical applications, therapeutic compounds can be suitably admixed in a pharmacologically inert topical carrier such as a gel, an ointment, a lotion or a cream. Such topical carriers include water, glycerol, alcohol, propylene glycol, fatty alcohols, triglycerides, fatty acid esters, or mineral oils. Other possible topical carriers are liquid petrolatum, isopropylpalmitate, polyethylene glycol, ethanol 95%, polyoxyethylene monolauriate 5% in water, sodium lauryl sulfate 5% in water, and the like. In addition, materials such as anti-oxidants, humectants, viscosity stabilizers and the like also may be added if desired.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

In addition to treatment of human subjects, the therapeutic methods of the invention also will have significant veterinary applications, e.g. for treatment of livestock such as cattle, sheep, goats, cows, swine and the like; poultry such as chickens, ducks, geese, turkeys and the like; horses; and pets such as dogs and cats. Also, the compounds of the invention may be used to treat non-animal subjects, such as plants.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines.

In general, compounds of the invention for treatment can be administered to a subject in dosages used in prior tetracycline therapies. See, for example, the *Physicians' Desk Reference*. For example, a suitable effective dose of one or more compounds of the invention will be in the range of from 0.01 to 100 milligrams per kilogram of body weight of recipient per day, preferably in the range of from 0.1 to 50 milligrams per kilogram body weight of recipient per day, more preferably in the range of 1 to 20 milligrams per kilogram body weight of recipient per day. The desired dose is suitably administered once daily, or several sub-doses, e.g. 2 to 5 sub-doses, are administered at appropriate intervals through the day, or other appropriate schedule.

It will also be understood that normal, conventionally known precautions will be taken regarding the administration of tetracyclines generally to ensure their efficacy under normal use circumstances. Especially when employed for therapeutic treatment of humans and animals in vivo, the practitioner should take all sensible precautions to avoid conventionally known contradictions and toxic effects. Thus, the conventionally recognized adverse reactions of gastrointestinal distress and inflammations, the renal toxicity, hypersensitivity reactions, changes in blood, and impairment of absorption through aluminum, calcium, and magnesium ions should be duly considered in the conventional manner.

Furthermore, the invention also pertains to the use of a tetracycline compound of formula I, for the preparation of a medicament. The medicament may include a pharmaceutically acceptable carrier and the tetracycline compound is an effective amount, e.g., an effective amount to treat a tetracycline responsive state.

In yet another embodiment, the invention also pertains to the use of a tetracycline compound of formula I to treat a tetracycline responsive state, e.g., in a subject, e.g., a mammal, e.g., a human.

Compounds of the invention may be made as described below, with modifications to the procedure below within the skill of those of ordinary skill in the art.

EXAMPLE 1

Synthesis of 13-Substituted Methacycline Compounds

General Procedure for Phenyl Boronic Acid Derivitization of Methacycline

Methacycline (1 equiv.), $PdCl_2$ (0.14 equiv.), and $CuCl_2$ (0.90 equiv.) were dissolved in 20 ml of MeOH and heated under nitrogen atmosphere. After 1 h, the boronic acid (2 equiv.) was added to it and the reaction mixture was heated for another 6–10 h. The reactions were either monitored by TLC, or analytical HPLC. Reaction mixture was then cooled down to the room temperature and was passed through a bed of celite. Evaporation of the solvent gave a yellow-brown solid in most of the examples, which was purified using preparative HPLC ($CH_3CN$:MeOH:$H_2O$). Evaporation of the solvent from the fractions indicated the right peak for the expected product, gave a yellow solid, which was again dissolved in MeOH and purged with HCl gas. After evaporation of MeOH, the yellow material was dried under vacuum for several hours.

EXAMPLE 2

Synthesis of 5-propionyl-13-(4'-chlorophenyl) methacycline 500 mg of 13-4'-Cl phenyl methacycline is dissolved in 20 ml of anhydrous HF. 3 ml of propionic acid is added and the reaction left for 2 days at room temperature. The HF was removed under a steady stream of $N_2$, and the residue triturated with $Et_2O$ to yield a dark yellow solid. The solid was dissolved in MeOH, and chromatographed on a divinyl benzene resin using an acetonitrile gradient from 30% to 100% with a primary solvent system of 0.1% formic acid. The corresponding fractions were collected and dried in vacuo to yield the product in overall 42%. The yellow solid was dissolved in MeOH and HCl gas bubbled in to produce the product as a yellow solid HCl salt.

EXAMPLE 3

Synthesis of 9,13-di-t-butyl methacycline 1.0 g of methacycline is added to 15 ml of concentrated $H_2SO_4$. 5 ml of isobutylene or t-butanol is added and the reaction stirred for 6 hours at room temperature. The reaction is neutralized with $Na_2CO_3$ (8 grams) and 40 ml of water, and the aqueous layer extracted 3× with 100 ml of N-butanol. The extracts were combined and dried to yield 69% of product as a light yellow solid. An analytical sample was obtained by the chromatography on divinyl benzene using a gradient of acetonitrile from 30–100% over 30 minutes against a primary solvent of 0.1% formic acid.

Physical Chemical Data for 13-substituted methacycline compounds

| | Rt (min) | MS(M + H) |
|---|---|---|
| 9-amino methacycline | | |
| 9,13-(di-t-butyl) methacycline | | |
| 13-(phenyl) methacycline | | 519.5 |
| 13-4'-(methoxyphenyl) methacycline | 9.15 | 549.5 |
| 13-4'-fluorophenyl) methacycline | | 537.5 |
| 13-4'-(chlorophenyl) methacycline | | 553.5 |
| 13-3'-(chlorophenyl) methacycline | | 553.5 |
| 13-(p-tolulylphenyl) methacycline | | 533.9 |
| 13-(3',4'-dichlorophenyl) methacycline | | 588.4 |
| 13-(4'-bromophenyl) methacycline | 11.05 | 597.3 |
| 13-($CF_3$-phenyl) methacycline | 11.24 | 587.5 |
| 13-(t-butyl) methacycline | 12.76 | 574.6 |
| 13-(4'-cyanophenyl) methacycline | 10.57 | 544.5 |
| 13-(4'-acetyl-phenyl) methacycline | 9.57 | 561.5 |
| 13-(3',5'-difluorophenyl) methacycline | 7.69 | 555.5 |
| 13-(3'-acetylphenyl) methacycline | | 561.5 |
| 13-(2',4'-difluorophenyl) methacycline | | 555.5 |
| 13-(3'-formylphenyl) methacycline | 9.98 | 547.5 |
| 13-(4'-$CO_2CH_3$)-phenyl) methacycline | 8.95 | 577.5 |
| 13-(3'-$NO_2$-phenyl) methacycline | 8.55 | 564.5 |
| 13-(2',3,4',5',6'-pentafluorophenyl) methacycline | | 609.4 |
| 13-(3',4'-methylenedioxophenyl) methacycline | 10.2 | 563.5 |
| 13-(4'-ethoxyphenyl) methacycline | | 563.5 |
| 13-4'-naphthylphenyl) methacycline | | 569.5 |
| 13-(2'-chlorophenyl) methacycline | | |
| 5-(propionyl)-13-(4'-chlorophenyl) methacycline | | |

EXAMPLE 4

In vitro Minimum Inhibitory Concentration (MIC) Assay

The following assay is used to determine the efficacy of tetracycline compounds against common bacteria. 2 mg of each compound is dissolved in 100 µl of DMSO. The solution is then added to cation-adjusted Mueller Hinton broth (CAMHB), which results in a final compound concentration of 200 µg per ml. The tetracycline compound solutions are diluted to 50 µL volumes, with a test compound concentration of 0.098 µg/ml. Optical density (OD) determinations are made from fresh log-phase broth cultures of the test strains. Dilutions are made to achieve a final cell density of $1 \times 10^6$ CFU/ml. At OD=1, cell densities for different genera should be approximately:

| | |
|---|---|
| E. coli | $1 \times 10^9$ CFU/ml |
| S. aureus | $5 \times 10^8$ CFU/ml |
| Enterococcus sp. | $2.5 \times 10^9$ CFU/ml |

50 µl of the cell suspensions are added to each well of microtiter plates. The final cell density should be approximately $5 \times 10^5$ CFU/ml. These plates are incubated at 35° C. in an ambient air incubator for approximately 18 hr. The plates are read with a microplate reader and are visually inspected when necessary. The MIC is defined as the lowest concentration of the tetracycline compound that inhibits growth. Compounds of the invention indicate good inhibition of growth.

Equivalents

Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

What is claimed is:

1. A 13-substituted methacycline compound of the formula:

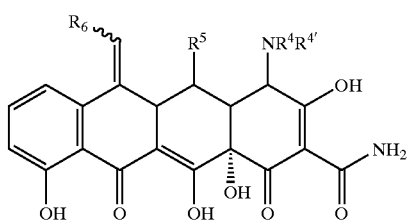

(I)

wherein:

$R^4$ and $R^{4'}$ are each alkyl;

$R^5$ is hydrogen, hydroxyl, or a prodrug moiety;

$R^6$ is an alkyl or an aryl group, and pharmaceutically acceptable salts thereof.

2. The 13-substituted methacycline compound of claim 1, wherein $R^5$ is hydroxyl.

3. The 13-substituted methacycline compound of claim 1, wherein $R^4$ and $R^{4'}$ are each methyl.

4. The 13-substituted methacycline compound of claim 1, wherein $R^6$ is alkyl.

5. The 13-substituted methacycline compound of claim 1, wherein $R^6$ is aryl.

6. A method for treating a tetracycline responsive state in a mammal, comprising administering to said mammal a 13-substituted methacycline compound, such that said tetracycline responsive state is treated, wherein said 13-substituted methacycline compound is of the formula:

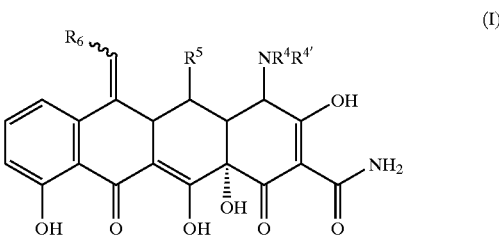

(I)

wherein:

$R^4$ and $R^{4'}$ are each alkyl;

$R^5$ is hydrogen, hydroxyl, or a prodrug moiety;

$R^6$ is an alkyl or an aryl group, and pharmaceutically acceptable salts thereof.

7. The method of claim 6, wherein said tetracycline responsive state is a bacterial infection.

8. The method of claim 7, wherein said bacterial infection is associated with *E. coli*.

9. The method of claim 7, wherein said bacterial infection is associated with *S. aureus*.

10. The method of claim 7, wherein said bacterial infection is associated with *E. faecalis*.

11. The method of claim 7, wherein said bacterial infection is resistant to other tetracycline antibiotics.

12. The method of claim 6, wherein said compound is administered with a pharmaceutically acceptable carrier.

13. A pharmaceutical composition comprising a therapeutically effective amount of a 13-substituted methacycline compound and a pharmaceutically acceptable carrier, wherein said 13-substituted methacycline compound is of the formula:

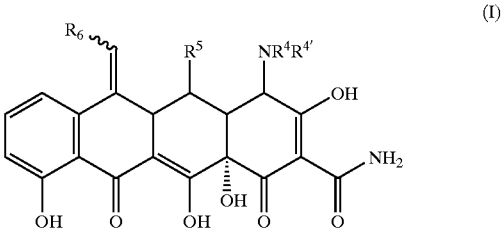

(I)

wherein:

$R^4$ and $R^{4'}$ are each alkyl;

$R^5$ is hydrogen, hydroxyl, or a prodrug moiety;

$R^6$ is an alkyl or an aryl group, and pharmaceutically acceptable salts thereof.

* * * * *